(12) United States Patent
Mengerink et al.

(10) Patent No.: US 9,630,374 B2
(45) Date of Patent: Apr. 25, 2017

(54) MULTILAYERED WOVEN MANUFACTURE AND USE OF THE MULTILAYER WOVEN MANUFACTURE AS CARRIERS FOR DRIED MATRIX SPOT APPLICATIONS

(71) Applicant: DSM IP ASSETS B.V., Heerlen (NL)

(72) Inventors: Ynze Mengerink, Echt (NL); Johannes Helena Michael Mommers, Echt (NL); Jun Qiu, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 43 days.

(21) Appl. No.: 14/368,178

(22) PCT Filed: Dec. 21, 2012

(86) PCT No.: PCT/EP2012/076688
§ 371 (c)(1),
(2) Date: Jun. 23, 2014

(87) PCT Pub. No.: WO2013/093024
PCT Pub. Date: Jun. 27, 2013

(65) Prior Publication Data
US 2015/0004360 A1   Jan. 1, 2015

(30) Foreign Application Priority Data
Dec. 22, 2011 (EP) .................................. 11195316

(51) Int. Cl.
*B32B 3/24* (2006.01)
*B32B 5/02* (2006.01)
(Continued)

(52) U.S. Cl.
CPC .............. *B32B 5/024* (2013.01); *B01L 3/508* (2013.01); *B32B 5/12* (2013.01); *B32B 5/26* (2013.01); *G01N 33/48* (2013.01); *G01N 33/5302* (2013.01); *B01J 20/28023* (2013.01); *B01J 20/28033* (2013.01); *B01J 20/28035* (2013.01); *B01J 20/28038* (2013.01);
(Continued)

(58) Field of Classification Search
None
See application file for complete search history.

(56) References Cited

U.S. PATENT DOCUMENTS 3,132,099 A * 5/1964 Eilhauer .............. B01D 39/083
156/155
3,552,928 A * 1/1971 Fetter ...................... C12Q 1/54
422/421

(Continued)

FOREIGN PATENT DOCUMENTS

EP      119623 A  * 10/1981
EP      226465 A2 *  6/1987
(Continued)

OTHER PUBLICATIONS

Machine Translation of JP 02243945 A, Sep. 1990.*
(Continued)

*Primary Examiner* — Jeff Vonch
(74) *Attorney, Agent, or Firm* — Nixon & Vanderhye P.C.

(57) ABSTRACT

The invention relates to a substantially laminary manufacture comprising 2 substantially laminary layers in contact, wherein the layers comprise a woven, hydrophilic material.

19 Claims, 2 Drawing Sheets

(51) Int. Cl.
  *B32B 5/12*     (2006.01)
  *B32B 5/26*     (2006.01)
  *G01N 33/48*    (2006.01)
  *B01J 20/28*    (2006.01)
  *G01N 33/53*    (2006.01)
  *B01L 3/00*     (2006.01)

(52) U.S. Cl.
  CPC .... *B01J 20/28052* (2013.01); *B01J 20/28054* (2013.01); *B01J 20/28095* (2013.01); *B01L 2200/12* (2013.01); *B01L 2300/069* (2013.01); *B01L 2300/0816* (2013.01); *B01L 2300/0874* (2013.01); *B01L 2300/0887* (2013.01); *B01L 2400/0406* (2013.01); *B32B 2250/20* (2013.01); *B32B 2262/0276* (2013.01); *B32B 2307/728* (2013.01); *Y10T 428/24074* (2015.01); *Y10T 428/24091* (2015.01); *Y10T 428/24099* (2015.01); *Y10T 428/24107* (2015.01); *Y10T 428/24124* (2015.01); *Y10T 428/24132* (2015.01); *Y10T 428/24322* (2015.01); *Y10T 428/24967* (2015.01); *Y10T 442/153* (2015.04); *Y10T 442/2484* (2015.04); *Y10T 442/3179* (2015.04); *Y10T 442/3472* (2015.04); *Y10T 442/3528* (2015.04); *Y10T 442/3667* (2015.04); *Y10T 442/3976* (2015.04)

(56) References Cited

U.S. PATENT DOCUMENTS

| | | | | |
|---|---|---|---|---|
| 3,607,093 A * | 9/1971 | Stone | B01D 61/38 | 422/422 |
| 3,690,606 A * | 9/1972 | Pall | B01D 39/12 | 210/510.1 |
| 3,701,433 A * | 10/1972 | Krakauer | A61M 1/3627 | 210/436 |
| 3,780,872 A * | 12/1973 | Pall | B01D 39/12 | 210/493.1 |
| 3,783,105 A * | 1/1974 | Moyer et al. | C12Q 1/32 | 422/510 |
| 3,802,842 A * | 4/1974 | Lange | C12Q 1/28 | 116/206 |
| 3,907,513 A * | 9/1975 | Sheinberg | B01D 29/01 | 428/549 |
| 4,046,514 A * | 9/1977 | Johnston | G01N 33/523 | 422/420 |
| 4,292,272 A * | 9/1981 | Kitajima | G01N 33/525 | 422/428 |
| 4,477,575 A * | 10/1984 | Vogel | B01D 39/2017 | 210/509 |
| 4,540,398 A * | 9/1985 | Barson | A61F 13/00987 | 604/1 |
| 4,668,472 A * | 5/1987 | Sakamoto | G01N 33/525 | 206/305 |
| 4,783,315 A * | 11/1988 | Arai | G01N 33/525 | 422/423 |
| 4,855,108 A * | 8/1989 | Masuda | G01N 33/525 | 210/500.21 |
| 4,916,059 A * | 4/1990 | Kageyama | G01N 33/526 | 435/15 |
| 4,994,238 A * | 2/1991 | Daffern | G01N 33/525 | 422/422 |
| 5,019,347 A * | 5/1991 | Hiratsuka | G01N 33/525 | 422/422 |
| 5,188,966 A * | 2/1993 | Eikmeier | G01N 33/525 | 422/504 |
| 5,215,716 A * | 6/1993 | Arai | G01N 33/525 | 422/423 |
| 5,258,163 A * | 11/1993 | Krause | G01N 33/525 | 422/401 |
| 5,290,515 A * | 3/1994 | Plesch | G01N 33/525 | 422/401 |
| 5,296,192 A * | 3/1994 | Carroll | G01N 33/525 | 422/408 |
| 5,783,277 A * | 7/1998 | Rock | B32B 5/26 | 2/258 |
| 5,846,837 A * | 12/1998 | Thym | G01N 33/521 | 422/423 |
| 5,876,389 A * | 3/1999 | Bouchard | A61B 10/0045 | 600/573 |
| 5,939,259 A * | 8/1999 | Harvey | C12N 15/1003 | 435/269 |
| 5,948,695 A * | 9/1999 | Douglas | B01L 3/5023 | 422/401 |
| 6,139,757 A * | 10/2000 | Ohmura | B01D 61/18 | 210/351 |
| 6,190,918 B1 * | 2/2001 | Chu | C12Q 1/54 | 422/408 |
| 6,231,815 B1 | 5/2001 | Bainczyk et al. | | |
| 6,309,546 B1 * | 10/2001 | Herrmann | B01D 39/12 | 210/490 |
| 6,555,061 B1 * | 4/2003 | Leong | G01N 33/526 | 422/412 |
| 6,669,905 B1 * | 12/2003 | Mathias | A61L 2/04 | 210/323.1 |
| 7,049,130 B2 * | 5/2006 | Carroll | G01N 33/525 | 422/408 |
| 8,691,098 B2 * | 4/2014 | Zambianchi | B01D 39/1623 | 210/459 |
| 2001/0051352 A1 * | 12/2001 | Krantz | G01N 33/525 | 435/14 |
| 2002/0173762 A1 * | 11/2002 | Ishikawa | A61F 13/53 | 604/385.01 |
| 2003/0031592 A1 * | 2/2003 | Knappe | G01N 33/525 | 422/423 |
| 2003/0175153 A1 | 9/2003 | Anaokar et al. | | |
| 2006/0201805 A1 * | 9/2006 | Forrow | C12Q 1/004 | 204/403.1 |
| 2008/0073294 A1 * | 3/2008 | Zambianchi | B01D 39/1623 | 210/767 |
| 2010/0252137 A1 | 10/2010 | Ueda | | |
| 2010/0254090 A1 * | 10/2010 | Trautman | F28D 15/046 | 361/704 |
| 2011/0004178 A1 * | 1/2011 | Fernkvist | A61F 13/15699 | 604/385.01 |
| 2012/0020839 A1 * | 1/2012 | Fuerst | B01L 3/5023 | 422/82.05 |
| 2013/0068043 A1 * | 3/2013 | Jung | C02F 1/004 | 73/864.91 |
| 2014/0127669 A1 * | 5/2014 | Hilder | C12M 45/22 | 435/2 |
| 2014/0329229 A1 * | 11/2014 | Lepene | G01N 33/543 | 435/5 |

FOREIGN PATENT DOCUMENTS

| | | |
|---|---|---|
| EP | 0 408 222 | 1/1991 |
| EP | 511120 A1 * | 10/1992 |
| EP | 934737 A1 * | 8/1999 |
| EP | 2 192 214 | 6/2010 |
| JP | 51025874 A * | 3/1976 |
| JP | 60222769 A * | 11/1985 |
| JP | 61-293398 | 12/1986 |
| JP | 01173868 A * | 7/1989 |
| JP | 02218957 A * | 8/1990 |
| JP | 02243945 A * | 9/1990 |
| JP | 3-130662 | 6/1991 |
| JP | 10-206298 | 8/1998 |
| JP | 2010-126848 | 6/2010 |
| WO | WO 9323755 A1 * | 11/1993 ............ B01L 3/5023 |

OTHER PUBLICATIONS

The First Office Action, CN Application No. 201280064010.0 (Apr. 16, 2015).
The Second Office Action, CN Application No. 201280064010.0 (Dec. 7, 2015).

(56) References Cited

OTHER PUBLICATIONS

International Search Report for PCT/EP2012/076688 mailed Apr. 8, 2013.
Notice of Reasons for Rejection, JP Patent Appln. No. P2014-548076, Oct. 25, 2016.
https://www.sefar.com/data/docs/fr/6780/FS-PDF-FC-CI-26-Medical-EN.pdf?20v=1.2.
http://techlist.sefar.com/cms/newstechlistpdf.nsf/vwWebPDFs/medifab_EN.pdf/$FILE/medifab_EN.pdf.

* cited by examiner

MULTILAYERED WOVEN MANUFACTURE AND USE OF THE MULTILAYER WOVEN MANUFACTURE AS CARRIERS FOR DRIED MATRIX SPOT APPLICATIONS

This application is the U.S. national phase of International Application No. PCT/EP2012/076688 filed 21 Dec. 2012 which designated the U.S. and claims priority to EP 11195316.2 filed 22 Dec. 2011, the entire contents of each of which are hereby incorporated by reference.

The present invention relates to a substantially laminary manufacture comprising 2 substantially laminary layers in contact, wherein the layers comprise a woven, hydrophilic material.

Dried blood spot (DBS) technology refers to a sampling method in which blood, obtained from e.g. a finger or heel prick, is spotted onto a carrier and dried. These dried blood spots can be analyzed e.g. after extraction by e.g. LC-MS/MS.

The main advantages of this sampling technique are (1) only a small amount (drop) of blood is required (2), blood can be obtained by a less invasive finger prick compared to a venapunction, (3) storage of dried spots is easy and no cooling is needed, (4) sending a dried blood spot can be done by postal mail, also cooling is not needed, (5) analytes are in general more stable in dried blood than in liquid blood. Given the fact that obtaining blood by performing a fingerprick, blood spotting and sending the dried spots by postal mail, are all fast and easy steps to perform, this technique can be performed by non-medically skilled persons, e.g. patients, themselves in a non-medical environment e.g. at home.

The main disadvantages are that (1) this technique can not be used for volatile compounds, (2) drying is required before sending and storing, (3) for most carriers, the spotted amount of blood (in μL) per carrier area depends on the blood's hematocrit value. This dependency has impact on the quantitative results when a defined area is punched from the blood spot for analytical purposes. The higher the hematocrit value, the higher the measured concentration, compared to blood having a lower hematocrit value.

The hematocrit dependency is recognized as a serious problem for the acceptance of DBS technology for some application fields e.g. in the field of pharma. Solutions for this problem are e.g. spotting a known fixed volume e.g. by using a (micro) capillary followed by the analysis of the whole spot. In this procedure a fixed blood volume is analyzed, independent of the blood's hematocrit value. The main disadvantage of this solution is the extra step that has to be performed, in this case the handling of a capillary and precise spotting. Especially for non-medically skilled persons who have to perform the fingerprick and blood spotting by themselves e.g. for therapeutic drugs monitoring, this extra step is a major disadvantage.

The present invention overcomes the hematocrit dependency by providing a substantially laminary manufacture comprising at least two substantially laminary layers in contact, wherein the layers comprise a woven, hydrophilic material.

Preferably, the invention provides said manufacture, wherein the laminary layers comprise material with a mesh opening between 11 and 800 μm and a layer thickness between 38 and 520 μm, an open area between 1 and 65%, a mesh count warp between 270 and 9 n/cm, a mesh count weft between 206 and 9 n/cm, a wire diameter warp and a wire diameter weft between 20 and 800 μm (preferably 24 and 480 μm). In particular, the manufacture, wherein the layers comprise material with a mesh opening between 20 and 200 μm and a layer thickness between 38 and 200 μm, an open area between 30 and 50%, a mesh count warp between 100 and 200 n/cm, a mesh count weft of between 100 and 200 n/cm, a wire diameter warp and a wire diameter weft both between 24 and 50 μm, and most particular the manufacture, wherein the layers comprise material with a mesh opening of about 40 μm and a layer thickness of about 38 μm, an open area of about 40%, a mesh count warp of about 158 n/cm, a mesh count weft of about 158 n/cm, a wire diameter warp and a wire diameter weft between of both about 24 μm. Typically, the two substantially laminary layers in contact consist of the same material, and if the manufacture comprises more substantially laminary layers, then it is preferred that all layers consist of the same material.

By wire diameter is herein meant the largest diameter of the material forming the wire of the weave. The wire may be a monofilament or a multifilament material. A wire diameter of 20 μm to 200 μm is preferred, as thinner wires are easier to cut when the dried matrix spot is later sampled by punching of the manufacture with the dried matrix spot, and hence more preferred are laminary layers with a wire diameter of 20 μm to 150 μm.

It was found that for very wide mesh openings the matrix may be lost during punching of the manufacture with the dried matrix spot. In a preferred embodiment, the mesh opening is hence at most 200 μm and more preferably the mesh opening is at most 125 μm. Very small mesh opening may lead to low absorption capacity and hence it is preferred that the mesh opening is at least 20 μm and more preferably at least 25 μm for substantial open area and blood cell access.

By open area is herein meant the percent of a layer of the layer that is not occupied by wire when observed orthogonally to the main surface. The open area may be calculated from the diameter of the wire and mesh opening taking into account variations between warp and weft directions if present. Open area is hence not related to the spacing between the laminary layers but to the individual layers.

By mesh opening is herein meant the maximum open distance between edges of adjacent warp wires and edges of adjacent weft wires. It is preferred that the mesh opening is the same in warp and weft directions, and if the mesh opening is not the same in the warp and the weft directions, then the mesh opening should indicate which direction is concerned.

The invention is hereinafter further illustrated with reference to the attached drawing in which.

The wires are typically polyester or polyamide. The wire should preferably be non-porous as it was found that this reduced the separation between blood cells and plasma during penetration of the manufacture. In one embodiment according to the invention, the wires are porous and the porous surface of the wires are at least partially covered by a coating, which coating preferably provides hydrophilic properties to the wires. Preferably, the surface of the wires are substantially covered or fully covered by the coating so the wires become non-porous wires.

In order to improve handleability of the manufacture according to the invention for example for DBS purposes, it is preferred that the manufacture further comprises a rigid, laminary passé partout or framework in contact with one of said layers, for example before or behind the layers. This passé partout typically comprises one or more holes, through which holes matrix material such as blood may be applied to the layers of the manufacture. This way, the manufacture can be used as a carrier for dried matrix spot applications. In one embodiment, said passé partout is in contact with two or more distinct substantially laminary manufactures comprising hydrophilic material, all of which are situated behind separate holes. This allows for more tests to be carried out on the same manufacture. The more tests can be repetition of the same test or different tests. Typical size of the holes is 1.5 cm to 4 cm. For DBS applications it is preferred that the size of the holes is about 2 cm to 3 cm.

In the context of the present invention, laminary means that the object, in this case the manufacture or layer, is significantly wider and broader than it is thick, in particular by a factor of 25, 50, 100 or more. Width and breadth do not have to be identical. By substantially laminary is meant that the thickness should be substantially the same over the surface area, but microscopic (less than 0.5 mm) thickness alterations or such which are not detrimental to the behavior exhibited by the present invention are acceptable. A preferred example for dimensions and their ratios of "substantially laminary" in the context of the present invention includes a credit card.

In the context of the present invention, a layer means one substantially laminary part of a larger system, which, microscopically or macroscopically, is distinguishable from other parts of the system by means of physical or chemical properties. Preferably, the manufacture comprises 2 to 18 layers arranged on top of each other in a stack. Two layers was found to be the minimum to realize proper catching of the blood and more that about 15 layers was found to be possible but not add any advantage and tended to complicate the manufacturing, hard to punch and tended to yield small blood spots. More preferably, the manufacture comprises at least 3 layers as this allows for a better interaction between the layers and still more preferably 4 to 12 layers, such as 8 to 12 layers. Most preferred was found to use about 8 or 4 layers in the manufacture of said material. In order to keep the manufacture from disintegrating, the layers are preferably kept in contact by laser welding, ultrasonic welding, punctual glue, by coating and curing, by partial melting, however, a mechanical fixing for example by using a rigid framework to hold the layers in contact. Such a rigid framework can also form part of a passé partout as described elsewhere herein.

The manufacture typically has a front surface adapted for receiving of fluid during use, and a back surface facing away from the front surface. It is preferred that the manufacture comprising at least three substantially laminary layers, and that the substantially laminary layers forming the front surface and/or the back surface have a lower mesh opening than at least one substantially laminary layer arranged between the substantially laminary layers forming the front surface and the back surface. This reduces the risk that matrix absorbed into the manufacture is lost through the front surface or the back surface and yet allows for a very large absorption capacity of the manufacture due to the large mesh opening in one or more of laminary layers arranged between the back surface and the front surface. Particularly, this embodiment may reduce or even prevent loss of dried matrix material during punching of the manufacture.

In one embodiment of the present invention, the woven material of the layers has a constant average open area.

In another embodiment, the manufacture has a front surface adapted for receiving of fluid during use, and a back surface facing away from the front surface and the back surface is impermeable for water. The back surface may be a further layer arrange at back surface, where this further layer is different from other layers in the manufacture; the impermeable back surface may be achieved by coating the back surface with a further coating or the impermeable back surface may be achieved by a (rigid) framing arranged at least partially around the manufacture. The impermeable back surface is not permeable for blood and acts as a stopping layer in the manufacture to prevent blood from exiting the manufacture on the side of the manufacture opposite to where blood is applied during use.

The weaving may be a plain weave (such as for example 1 over 1, and 2 over 2), twill weave (such as 2/2 twill, 2/1 twill, 1/2 twill, 3/3 twill) or another type of weave. For manufactures according to the invention, plain weave is preferred. In the context of the present invention, hydrophilic material means that a droplet of 20 µm of water is absorbed into a manufacture comprising the material within 5 s. It was found that this was a suitable definition to ensure that two closely spaced coaxial surfaces of substantially laminary layers of a manufacture according to the invention will enhance a laminar flow of biologic aqueous matrices like blood. Hydrophilicity can be achieved by a material that is hydrophilic by itself or has been made hydrophilic by coating with a hydrophilic material. Typically, polyester (PET) or polyamide (PA) are used as wires for the laminary layer and more preferably the wires are coated with a PEG based coating. Preferably, the coating material is cured to reduce extractables and leachables. A coating composition which fulfills these criteria is commercially available under the name VitroStealth® from DSM, Netherlands, which coating composition is described in United States Patent Application 20110263011.

The hydrophilization coating may be applied onto the laminary layers by any process known in the art of wet coating deposition in one or multiple steps. Examples of suitable processes are spin coating, dip coating, spray coating, flow coating, meniscus coating, capillary coating and roll coating, aspiration coating, kiss coating, or suitable combinations thereof. In one embodiment, the coating is used solely for increasing the hydrophilicity of the laminar layers. In another embodiment, the coating is used for a combination of increasing the hydrophilicity of the laminar layers as well as for connecting the layers to each other.

In the context of the present invention, in contact means that the flat surfaces of two objects are brought together and held together on a macroscopic level. This can for example be achieved by a passé partout described elsewhere in this document. It is not necessary to bring and hold the area where the biological sample is spotted together on a microscopic, i.e. molecular or atomic, level, e.g. my means of an adhesive bond such as glue. On the contrary, in the context of the present invention such substantial adhesive bond might interfere with assumed capillary forces within the manufacture. The optional coating of the wires or the laminary layers may create the contact between the laminary layers. In this case it is highly preferred that the coating is present in a low amount so a limited part of the open area of the laminary layers is filled with the coating.

Without being bound by theory, it is believed that during use the meshes (open spaces) of the woven material are fully filled will blood, so that the blood volume per carrier area is a fixed. The multilayers ensure a lateral flow of the spotted blood between the layers resulting in a circular blood spot within which all meshes of all layers are completely filled with blood.

An embodiment of the manufacture particularly suitable for dried blood spot applications has a front surface adapted for receiving of fluid during use. The area of a 30 µl, 80% hematocrit blood sample on the surface after drying 2 hours at 20° C. in air is referred to as the area, A1, of the first dried blood spot, and the area of a 30 μl, 20% hematocrit blood sample on the surface after drying 2 hours at 20° C. in air is referred to as the area, A2, of the second dried blood. The area difference, ΔA, is the numerical value of A1−A2 divided by A1, i.e.: ΔA=|A1−A2|/A1. It was found that the manufacture of the invention was particularly useful when the area difference ΔA<20%, preferably ΔA<15%, more preferably ΔA<10%, and most preferably ΔA<8%. ΔA is calculated based on the average size of three different spot for both hematocrit values.

In a highly preferred embodiment, at least two of the substantially laminary layers are rotated relative to each other by an angle. By rotated by an angle is here meant that while the layers remains substantially parallel in the stack of layers the rotated layer will have a different direction of the warp wire than the non-rotated layer, which angle is referred to as $v_{nm}$, where n and m indicates the relative layer position. $V_{12}$ is hence the angle between adjacent layers and $v_{13}$ is hence the angle between layers separated by one layer. It was found to be highly advantageous that a first of the two substantially laminary layers is rotated by an angle, $v_{12}$, to a second of the two substantially laminary layers, and the angle, $v_{12}$, is 7° to 83°; preferably the angle, $v_{12}$, is 10° to 80°, and more preferably the angle, $v_{12}$, is 13° to 77°. For very low rotation angles, the dried matrix spot tended to create raster areas i.e. areas where the matrix material was concentrated, and hence leading to a very inhomogeneous distribution of the matrix material, such as blood. The spacing of the rasters depends on the spacing of the mesh as well as the angle of rotation between adjacent layers and seems to follow a moiré-like pattern. Particularly, it was found that at higher angles of rotation the distance between rasters became so small (for example below 0.5 mm or below 0.3 mm) that the effect was not observed in practice as the rasters would be too close. It could be theorized without being limited thereto that the geometry of the raster corresponds to two dimensional moiré-like patterns. The larger and sometimes inhomogeneous dried blood spots observed sometimes for manufactures with $v_{12}$=0° may be caused by certain meshes or areas of the manufacture not being filled due to blocking of such areas and as a consequence, larger inhomogeneous spots are observed. All in all, this meant that a deliberate and substantial rotation between the layers of the manufacture lead to consistently more reproducible dried matrix spot formation, whereas small variations such as 1-3° (which may easily arise during preparation of manufactures intended to be arranged with zero rotation angle unless substantial care is used) may lead to very inhomogeneous spot formation.

In a particularly advantageous embodiment, the manufacture comprises a third substantially laminary layer connected to the second of the two substantially laminary layers (i.e. on the other side than the first substantially laminary layer) and the third substantially laminary layer is rotated by an angle, $v_{23}$, to the second of the two substantially laminary layers. It was found that when the angle, $v_{23}$, is substantially the same magnitude and opposite direction than the angle $v_{12}$, an easily producible manufacture was realized while the advantage of utilizing rotated layers was maintained. In this situation, the angle, $v_{13}$, between the first of the two substantially laminary layers and the third substantially laminary layer is about zero. In other words, the substantially laminar layers of the manufacture are arranged as A-B-A-B . . . , where layers 1, 3 . . . are arranged with the warp wire in the same (A) direction and layers 2, 4, . . . are arranged with the warp wire in same direction (B) different the direction (A).

In another embodiment, the manufacture comprises a third substantially laminary layer connected to the second of the two substantially laminary layers (i.e. on the other side than the first substantially laminary layer) and the third substantially laminary layer is rotated by an angle, $v_{23}$, to the second of the two substantially laminary layers. In this embodiment, the angle, $v_{13}$, between the first of the two substantially laminary layers and the third substantially laminary layer as well as the angle $v_{23}$ are 7° to 83°; preferably the angles $v_{13}$ and $v_{23}$ are 10° to 80°, and more preferably the angles $v_{13}$ and $v_{23}$, are 13° to 77°. It was found that this embodiment reduced any moiré-like effect of the pattern further leading to more reproducible dried matrix spots. In other words, the substantially laminar layers of the manufacture are arranged as A-B-C-D . . . , where at least layers 1, 2, and 3 are arranged with the warp wire in different directions. The present manufacture is also suitable for other types of dried spot applications than dried blood spot applications. Such applications are also referred to as dried matrix applications, where matrix refers to that the absorbed material may be blood as well as other aqueous solutions or suspensions of organic and/or inorganic material, such as for example water samples (such as drinking water, waste water, or process water); and food samples (such as fruit juices, wine, jam, apple sauce, milk (products)). Even thou dried blood spot applications are a highly preferred and particularly advantageous application of the manufactures of the present invention, it should hence be understood that dried matrix spot applications are also encompassed in the present invention. The expressions dried matrix spot and dried blood spot are used interchangeably in the present document unless specific circumstances show that particular embodiments are only directed to dried blood spot applications (such as advantages related to hematocrit value indifference).

An individual feature or combination of features from an embodiment of the invention described herein, as well as obvious variations thereof, are combinable with or exchangeable for features of the other embodiments described herein, unless the person skilled in the art would immediately realize that the resulting embodiment is not physically feasible.

EXAMPLES

Example 1

A) Whole fresh blood was centrifuged and the separated plasma and red blood cells were used to prepared blood mixtures having hematocrit values levels of 0, 20, 30, 40, 45, 50, 60, 70 and 80%.

B) A woven polyester material with a mesh opening of about 40 μm and a layer thickness of about 38 μm, an open area of about 40%, a mesh count warp of about 158 n/cm, a mesh count weft of about 158 n/cm, a wire diameter warp and a wire diameter weft of both about 24 μm, commercially available from Sefar (Switzerland) under the name Medifab (polyester) 07-40/40 (product number 3053-1000-843-V1, charge 3088149-00) was provided. The polyester wires of the mesh were non-porous wires, but hydrophilic. The desired layers of mesh material was assembled at the desired angle between the layers with a clip and dip-coated with a 2% coating composition comprising nanoparticles being grafted with reactive groups and hydrophilic polymer chains (commercially available under the name VitroStealth® commercially available from DSM, Netherlands). After drying, the manufacture was hydrophilic.

Example 2

Blood mixtures having hematocrit levels of 30, 50 and 70% was prepared by pipetting different volume rations of red blood cells and plasma.

For this example 20 µl of blood having hematocrit values of 30, 50 and 70% was spotted onto 3-layered manufactures manufacture as described in Example 1-B. The average spot diameter for HT 30% and 50% is 18 mm and for 70%, 19 mm. From these results it is therefore surprisingly concluded that different hematocrit values of 30, 50 and 70 has no significant influence on the spot diameter when spotting a fixed volume of 20 µL of blood.

Example 3

Blood mixtures having hematocrit levels of 0, 20, 30, 40, 50, 60, 70 and 80% was prepared as in Example 1A. For this example 20 µl or 50 µl of blood was spotted onto 4-layered manufactures manufactured as described in Example 1-B with zero rotation between adjacent layers or uncoated assemblies of four layers of cellulose based material, respectively, where the manufactures where held together mechanically between a backing and a front passé partout. After drying, the blood spot diameters were measured.

The results of the spot diameters obtained for the 4-layer of manufacture of Example 1-B and the cellulose based material are given in table 1. The results in table 1 clearly indicate that there is no measurable difference between the spot diameters when spotting blood with different hematocrit values from 0 (plasma) to 80% onto the 4-layer manufacture according to the invention as prepared in Example 1-B whereas a large significant difference (>50%) in spot diameters is observed for the cellulose based material. This result clearly indicates that the volume per area is constant for the 4-layer manufacture of Example 1-B and not constant for the cellulose based material.

TABLE 1

|  | Spot Diameter (mm) | |
| --- | --- | --- |
| Hematocrit % | 4 layers of Example 1-B (example) | Cellulose based material (comparative example) |
| 0 | 16 | 17 |
| 20 | 16 | 15 |
| 30 | 16 | 14 |
| 40 | 16 | 13 |
| 50 | 16 | 12 |
| 60 | 16 | 12 |
| 70 | 16 | 12 |
| 80 | 16 | 11 |

Example 4

This example shows the influence of the number of layers on the blood spot diameter.

A constant volume of blood having a hematocrit level of approximately 45% was spotted onto a 4, 6, 8, 10 and 12-layered manufactures prepared as described in Example 1-B with zero angle between adjacent layers. After drying, the blood spot diameters were measured. The results are given in table 2.

TABLE 2

Influence of number of layers on blood spot diameter

| Number of layers of manufacture of Example 1-B | Spot diameter/mm |
| --- | --- |
| 4 | 20 |
| 6 | 16 |
| 8 | 14 |
| 10 | 12 |
| 12 | 10 |

The results clearly indicate a relation between number of layers and spot diameter or spot area. In general it can be observed that the spot size is directly related to the sum of the volume in the open area of the layers and the volume between the layers. As a consequence, the blood volume per area (which could be a requirement for certain applications) is adjustable simply by changing the number of layers.

Example 5

This example shows the influence of blood spotting volume on the blood spot diameter.

Blood volumes of 10, 20 30 and 40 µL were spotted onto 4-layered manufactures prepared as described in Example 1-B with zero rotation between layers. After drying, the blood spot diameters were measured. The results are given in table 3.

TABLE 3

| Blood volume µL | Spot diameter mm |
| --- | --- |
| 10 | 11 |
| 20 | 16 |
| 30 | 20 |
| 40 | 24 |

The results clearly indicate, as expected, a quadratic relation between the spotted blood volume and the spot diameter.

Example 6

Manufactures with five different materials (Mesh opening, Open Area and wire diameter (same warp and weft mesh opening and wire diameter)) were tested with respect to their hematocrit dependency. All cards were prepared as described in Example 1B with 8 layers of polyester and adjacent layers were oriented 45° towards each other in an ABAB . . . stack. The cards were dip coated with 2% VitroStealth® coating composition and cured in the paper passé partout. 30 µl blood mixtures with a hematocrit value of 20%, 45% and 80%, respectively, was applied to 2 to 8 manufactures per hematocrit, whereafter the spots were allowed to dry. The dried spot size area was measured and the standard deviation of dried spot size area was calculated. The results are shown in TABLE 4. For all the investigated materials, the standard deviation was ≤8%.

TABLE 4

| | Mesh opening μm | Open Area % | fiber diameter μm | Spot size Ht 20 mm2 | Spot size Ht 45 mm2 | Spot size Ht 80 mm2 | dA (Ht80-Ht20) % | Norm Spot size Ht20 (Ht45 = 1) | Norm Spot size Ht45 (Ht45 = 1) | Norm Spot size Ht80 (Ht45 = 1) | Spot size avg mm2 | RSD % |
|---|---|---|---|---|---|---|---|---|---|---|---|---|
| Material 1 | 20 | 13 | 37 | 120 | — | 108 | 10 | 1.05 | | 0.95 | 111 | 8 |
| Material 2 | 100 | 32 | 77 | 50 | 56 | 50 | 0 | 0.89 | 1.00 | 0.89 | 52 | 5 |
| Material 3 | 51 | 33 | 38 | 101 | 101 | 89 | 12 | 1.00 | 1.00 | 0.88 | 98 | 7 |
| Material 4 | 40 | 40 | 24 | 153 | 152 | 150 | 2 | 1.00 | 1.00 | 0.99 | 152 | 7 |
| Material 5 | 190 | 70 | 33 | 69 | 78 | 73 | 6 | 0.89 | 1.00 | 0.94 | 75 | 4 |

It is observed that there were no significant differences in dried blood spot size observed within each specific material with respect of the hematocrit values of the spotted blood samples.

Example 7

Three different manufactures with orientated layers were prepared by the method described in Example 1B of polyester woven material with a mesh opening of 40 μm, 40% open area and 24 μm wire diameter. 8 layers were used for the manufactures and the layers were assembled and dip-coated to form the manufacture. Layers $3^{rd}$, $5^{th}$ and $7^{th}$ layers were oriented as the $1^{st}$ layer (so at an angle of 0° relative to $1^{st}$ layer, i.e. $v_{13}$=0°). The $2^{nd}$, $4^{th}$, $6^{th}$ and $8^{th}$ layers were all oriented relative to the $1^{st}$ layer with the same angle, $v_{12}$. Three manufactures with $v_{12}$=0°, $v_{12}$=15° and $v_{12}$=45°, respectively were prepared. All manufactures were spiked with 30 μl blood of same hematocrit value. Results are shown in TABLE 5. The manufactures with $v_{12}$=0° (i.e. all layers oriented in parallel) showed larger spot sizes and an inhomogeneous distribution of dried blood. The manufactures with $v_{12}$=15° and $v_{12}$=45° show very homogeneous distribution of the dried blood and formed round dried blood spots. Furthermore, the manufacture with $v_{12}$=0° showed larger spot sizes compared to the orientated layers ($v_{12}$=15° and $v_{12}$=45°).

seen for rotation angles of $v_{12}$<about 10° where very distinct pattern of spots with overlapping mesh openings surrounded by regions closed by overlapping or parallel wires was observed. It could be theorized (without being limited thereto) that the spots may corresponds raster from time to time appearing on manufactures after drying of blood spots. For larger values of $v_{12}$ the distance between the spots of overlapping mesh openings become very short as for example shown for $v_{12}$ of 15° and surprisingly will not influence the spot formation whereas for lower values of $v_{12}$ distance between spot become very large and very inhomogeneous spot formation may appear unless extreme care is taken during aligning of the layers. For very large rotation angles (here shown for $v_{12}$=45°) no raster formation was observed. It appears that the geometry of the raster corresponding to two dimensional moiré-like patterns (see figure below). The larger and sometimes inhomogeneous dried blood spots observed sometimes for manufactures with $v_{12}$=0° may be caused by certain meshes or areas of the manufacture not being filled due to blocking of such areas and as a consequence, larger inhomogeneous spots are observed. The orientation does not seem to influence the hematocrit independent behavior of the material.

Example 9

Influence of relative orientation between layers (rotation angle $v_{12}$) on homogeneity of dried matrix spots were

TABLE 5

| Orientation o | Mesh opening μm | Open Area % | fiber diameter μm | Spot size Ht 20 mm2 | Spot size Ht 45 mm2 | Spot size Ht 80 mm2 | Norm Spot size Ht20 (Ht45 = 1) | Norm Spot size Ht45 (Ht45 = 1) | Norm Spot size Ht80 (Ht45 = 1) | spot size avg mm2 | RSD % | n % |
|---|---|---|---|---|---|---|---|---|---|---|---|---|
| 45 | 40 | 40 | 24 | 153 | 152 | 150 | 1.00 | 1.00 | 0.99 | 152 | 7 | 8 |
| 15 | 40 | 40 | 24 | 163 | 161 | 151 | 1.00 | 1.00 | 0.94 | 160 | 8 | 8 |
| 0 | 40 | 40 | 24 | — | 191 | 187 | | 1.00 | 0.98 | 189 | 8 | 8 |

Example 8

Figure 1:
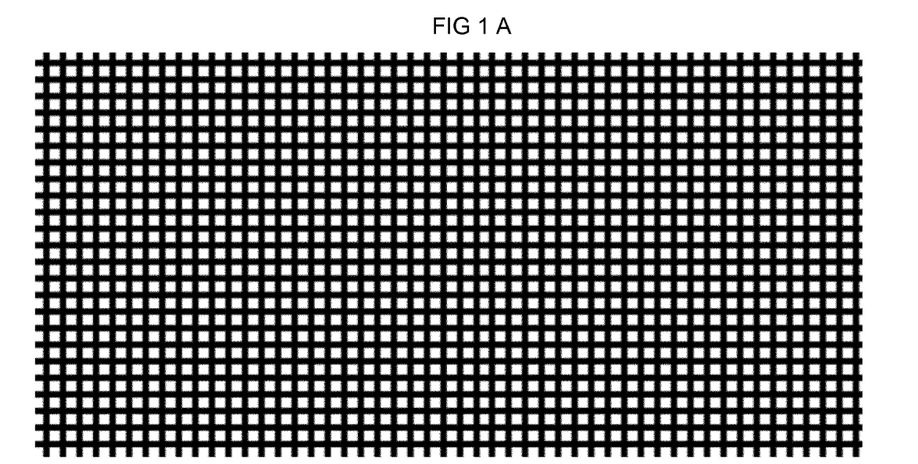
FIG. 1 shows examples of results of simulations described in Experiment 8.
Figure 1C:
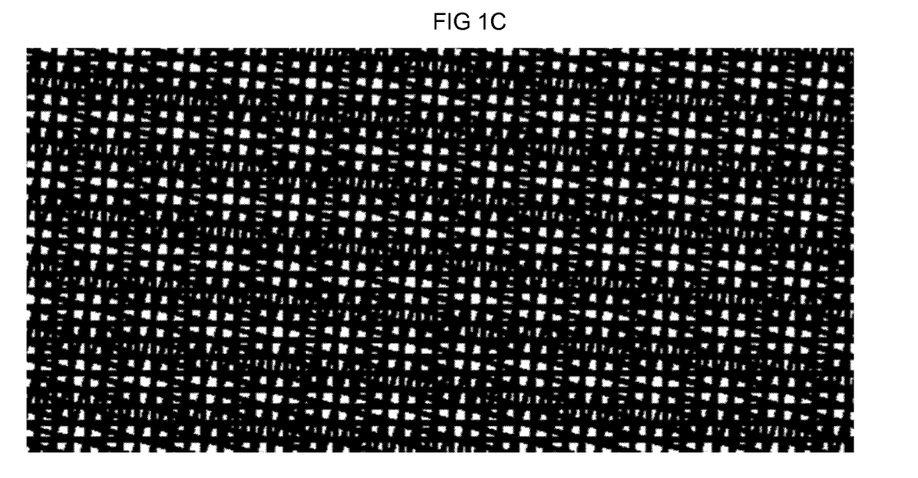
Figure 1D:
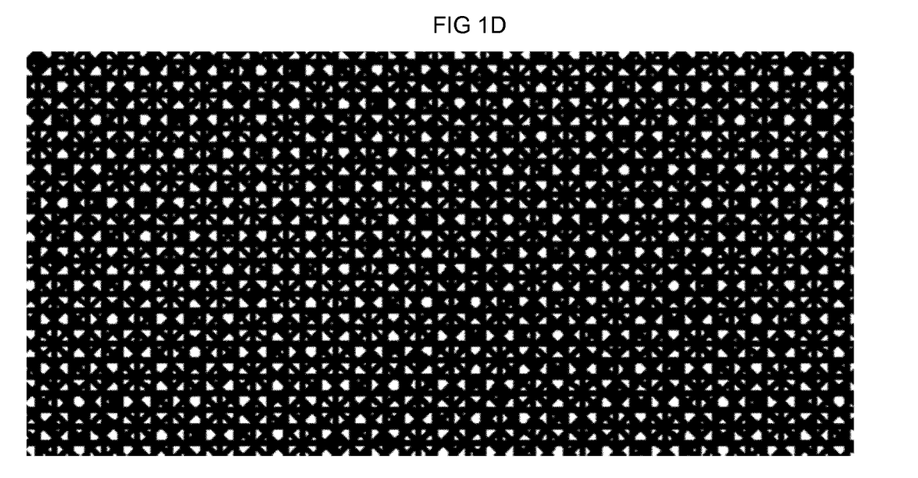

A mesh with parameters close to those of the mesh used in Example 7 (here using mesh opening 40 μm and wire diameter 25 μm in both warp and weft directions) was simulated for angles $v_{12}$ of 0°, 3°, 15° and 45°. Plots of the modeled manufactures are shown in FIG. 1. Each plot corresponds to an area of about 1.5×3 mm. In FIG. 1A) it is observed that perfect alignment of the mesh (corresponding to $v_{12}$=0°) leads to a perfect grid. However, even a small deviation as $v_{12}$=3° (see FIG. 1B) will lead to very clear formation of areas with very different transparency for the matrix (also herein referred to as rasters) separated by large distances of here about 1-2 mm. Similar observations are investigated using Liquid chromatography tandem mass spectrometry LCMSMS. Identical volumes of codeine spiked blood (Ht=45) were spotted on manufactures according to the invention. Each manufacture had 8 substantially laminary layers arranged with different angles between adjacent layers without layer orientation. Three manufactures with $v_{12}$=0°, $v_{12}$=15° and $v_{12}$=45°, respectively. For all manufactures were used $v_{13}$=0° (In other words, the layers were oriented as ABAB ... ). For each manufacture six spots were made and of each spot three different punches were analyzed with LCMSMS to establish codeine content. It was observed that the 45° orientation layers yielded the best (lowest) standard deviation, namely RSD 5%, (See TABLE 6).

TABLE 5

| Orientation ° | Mesh opening μm | Open Area % | fiber diameter μm | RSD LCMSMS Codeine in blood (Ht45) % |
|---|---|---|---|---|
| 45 | 40 | 40 | 24 | 5 |
| 15 | 40 | 40 | 24 | 7 |
| 0 | 40 | 40 | 24 | >10 |

The invention claimed is:

1. A carrier for dried blood spot applications comprising a substantially laminar manufacture having a front surface adapted for receiving blood during use comprising at least two substantially laminar layers in contact, wherein the layers each comprise meshes of woven, hydrophilic material, and wherein at least two of the layers are rotated relative to each other by an angle $v_{nm}$ of 7° to 83°, wherein n and m indicate relative layer positions, and wherein upon blood spotting the meshes of at least two layers are filled with blood forming a blood spot with a substantially fixed volume of blood per carrier area, and wherein an area difference, $\Delta A$, between a first dried blood spot and a second dried blood spot is less than 20%, where the area of the first dried blood spot is the area of a 30 μl 80% hematocrit blood sample on the surface after drying 2 hours at 20° C. in air and the area of the second dried blood spot is the area of a 30 μl 20% hematocrit blood sample on the surface after drying 2 hours at 20° C. in air.

2. The carrier according to claim 1, wherein the area difference, $\Delta A$, between a first dried blood spot and a second dried blood spot is less than 10%.

3. The carrier according to claim 1, wherein the at least two layers each comprise material with a mesh opening between 11 μm and 800 μm, a layer thickness between 38 μm and 520 μm, an open area between 1% and 65%, a mesh count warp between 270 n/cm and 9 n/cm, a mesh count weft of between 206 n/cm and 9 n/cm, a wire diameter warp and a wire diameter between 24 μm and 480 μm.

4. The carrier according to claim 1, wherein the at least two layers each comprise material with a mesh opening between 20 μm and 200 μm, a layer thickness between 38 μm and 200 μm, an open area between 30% and 50%, a mesh count warp between 100 n/cm and 200 n/cm, a mesh count weft of between 100 n/cm and 200 n/cm, a wire diameter warp and a wire diameter between 24 μm and 50 μm.

5. The carrier according to claim 1, wherein the at least two layers each comprise material with a mesh opening of about 40 μm, a layer thickness of about 38 μm, an open area between 40%, a mesh count warp between 158 n/cm, a mesh count weft of between 158 n/cm, a wire diameter warp and a wire diameter between 24 μm.

6. The carrier according to claim 1, wherein the at least two layers each consist of the same material.

7. The carrier according to claim 1, the substantially laminar manufacture comprises 2 to 18 layers of the material.

8. The carrier according to claim 1, the substantially laminar manufacture comprises 4 to 12 layers of the material.

9. The carrier according to claim 1, wherein the at least two layers are kept in contact by laser welding, ultrasonic welding, punctual glue, laminar glue, or by using a rigid framework.

10. The carrier according to claim 1, further comprising a rigid, laminar sheet or framework in contact with one of the at least two layers.

11. The carrier according to claim 10, wherein the sheet comprises one or more holes.

12. The carrier according to claim 10, wherein the carrier comprises two or more of the manufactures and wherein the sheet is in contact with the two or more manufactures, wherein all of the manufactures are situated behind the holes.

13. The carrier according to claim 1, wherein a first of the at least two substantially laminar layers is rotated by an angle, $v_{12}$, relative to a second of the at least two substantially laminar layers, and the angle, $v_{12}$, is 7° to 83°.

14. The carrier according to claim 13, wherein the angle, $v_{12}$, is 10° to 80°.

15. The carrier according to claim 13, comprising a third substantially laminar layer connected to the second substantially laminar layer and the third substantially laminar layer is rotated by an angle, $v_{23}$, relative to the second substantially laminar layer, and the angle, $v_{23}$, is substantially the same magnitude in the opposite direction of the angle $v_{12}$ so that the angle, $v_{13}$, between the first substantially laminar layer and the third substantially laminar layer is about zero.

16. The carrier according to claim 13, comprising a third substantially laminar layer connected to the second substantially laminar layer and the third substantially laminar layer is rotated by an angle, $v_{23}$, relative to the second substantially laminar layer, whereby the angle, $v_{13}$, between the first substantially laminar layer and the third substantially laminar layer, as well as the angle $v_{23}$ are 7° to 83°.

17. The carrier according to claim 16, wherein the angles $v_{13}$ and $v_{23}$ are 10° to 80°.

18. The carrier according to claim 1, the substantially laminar manufacture having a back surface facing away from the front surface, wherein the back surface is impermeable for water.

19. The carrier according to claim 1, the substantially laminar manufacture having a back surface facing away from the front surface, and the substantially laminar manufacture comprising at least three substantially laminar layers, wherein substantially laminar layers forming the front surface and/or the back surface have a lower mesh opening than at least one substantially laminar layer arranged between the substantially laminar layers forming the front surface and the back surface.

* * * * *